United States Patent
Ahn

(10) Patent No.: US 10,591,397 B2
(45) Date of Patent: Mar. 17, 2020

(54) APPARATUS AND SYSTEM FOR CLASSIFYING PARTICLES

(71) Applicant: Industry-University Cooperation Foundation Hanyang University Erica Campus, Ansan-si, Gyeonggi-do (KR)

(72) Inventor: Kang Ho Ahn, Seoul (KR)

(73) Assignee: Industry-University Cooperation Foundation Hanyang University Erica Campus, Ansan-si, Gyeonggi-do (KR)

( * ) Notice: Subject to any disclaimer, the term of this patent is extended or adjusted under 35 U.S.C. 154(b) by 303 days.

(21) Appl. No.: 15/551,479

(22) PCT Filed: Feb. 17, 2015

(86) PCT No.: PCT/KR2015/001613
§ 371 (c)(1),
(2) Date: Aug. 16, 2017

(87) PCT Pub. No.: WO2016/133231
PCT Pub. Date: Aug. 25, 2016

(65) Prior Publication Data
US 2018/0067034 A1   Mar. 8, 2018

(51) Int. Cl.
*G01N 27/62* (2006.01)
*G01N 15/02* (2006.01)
(Continued)

(52) U.S. Cl.
CPC ....... *G01N 15/0266* (2013.01); *B01D 53/002* (2013.01); *B03C 3/36* (2013.01);
(Continued)

(58) Field of Classification Search
CPC .... B01D 2258/06; B01D 53/002; B03C 3/36; B03C 3/40; B03C 7/02; G01N 15/0266; G01N 2015/0046
See application file for complete search history.

(56) References Cited

U.S. PATENT DOCUMENTS 3,413,545 A * 11/1968 Whitby .............. G01N 15/0266
324/71.1
5,973,904 A * 10/1999 Pui ........................ B05B 5/0533
361/225
(Continued)

FOREIGN PATENT DOCUMENTS

JP          07-083820 A    3/1995
KR    10-2008-0081022 A    9/2008
(Continued)

*Primary Examiner* — Vinh P Nguyen
(74) *Attorney, Agent, or Firm* — Novick, Kim & Lee, PLLC; Jae Youn Kim

(57) ABSTRACT

Provided are an apparatus and a system for classifying particles. The apparatus for classifying particles includes: an internal electrode which has a column shape; an external electrode which is spaced apart from the internal electrode and disposed to surround the internal electrode, and generates an electric field through an interaction with the internal electrode; and an aerosol supply unit which supplies aerosol particles to a separation space between the internal electrode and the external electrode, in which the separation space, through which the aerosol particles are introduced into the particle classifying apparatus and flow, is formed to be narrowed toward a lower aerosol flow side from an upper aerosol flow side into which the aerosol particles are introduced.

14 Claims, 12 Drawing Sheets

(51) Int. Cl.
  *B01D 53/00* (2006.01)
  *B03C 3/36* (2006.01)
  *B03C 3/40* (2006.01)
  *G01N 15/00* (2006.01)
  *B03C 7/02* (2006.01)

(52) U.S. Cl.
  CPC ............ *B03C 3/40* (2013.01); *B01D 2258/06* (2013.01); *B03C 7/02* (2013.01); *G01N 2015/0046* (2013.01)

(56) References Cited

U.S. PATENT DOCUMENTS

| | | | |
|---|---|---|---|
| 6,230,572 B1 * | 5/2001 | Pui ........................ | B82Y 15/00 73/863.21 |
| 7,213,476 B2 | 5/2007 | Cheng et al. | |
| 7,880,109 B2 * | 2/2011 | Okuda ............... | G01N 15/0266 209/129 |

FOREIGN PATENT DOCUMENTS

| KR | 10-0865712 B1 | 10/2008 |
|---|---|---|
| KR | 10-2014-0114926 A | 9/2014 |

* cited by examiner

APPARATUS AND SYSTEM FOR CLASSIFYING PARTICLES

TECHNICAL FIELD

The present invention relates to an apparatus and a system for classifying particles, and more particularly, to an apparatus and a system for classifying particles which are capable of classifying particles according to the size and measuring distribution of particles by using a phenomenon in which a degree to which the particle is moved varies depending on a size of the particle when an electric field is applied.

BACKGROUND ART

In general, the measurement of particles existing in a clean space, such as a clean room for a process of producing a semiconductor, is a very important factor for the process of producing the semiconductor, and a technology capable of measuring even a nanoscale particle is required as a line width of the semiconductor is decreased in accordance with the development of the semiconductor technology. In addition, recently, as a technology using particles with nanometer to micrometer-sized structures has been developed, a technology, which not only measures ultrafine particles but also classifies the particles according to the size, is considered as a basic condition for researches.

As such, a need for technologies for measuring, evaluating, and classifying the particles is increased in various fields, and recently, the development is being actively conducted on an electrical particle classifying apparatus (different mobility analyzer (DMA)) which classifies the particles based on a difference in mobility of the particles caused by electrostatic force.

In this case, a typical DMA is configured to use a method of scanning voltage in order to measure the distribution of sizes of particles in an aerosol, and a scanning time of about two minutes is generally required, such that a large amount of time is required to classify the particles. In the case of researches on emission of air pollutants, particularly, soot and smoke produced by a diesel engine, it is nearly impossible to measure emission characteristics of the soot and smoke by using the existing DMA because sizes and concentration of the soot and smoke often vary in a very short period of time. A multi-system for classifying particles (multi-stage differential mobility analyzer (MDMA)) has been proposed as an alternative for the DMA. The MDMA includes a cylindrical high-voltage electrode installed in an aerosol flow direction, and several ports (ring electrodes) adjacent to the cylindrical high-voltage electrode, and the MDMA is configured to capture a particle having a comparatively small size at an initial part of an aerosol flow path, and capture a particle having a comparatively large size at a rear end of the aerosol flow path, thereby reducing the scanning time.

However, the MDMA has a drawback in that a very long length of the aerosol flow path needs to be ensured in order to capture even the particle having a large size, and as a result, an overall size of the apparatus is greatly increased, which leads to inefficiency. A method of increasing applied voltage has been proposed to solve the aforementioned problem, but this method has a problem in that reliability in classifying the particles deteriorates because the particle having a large size may also be captured at the initial part of the aerosol flow path when the applied voltage is high.

In addition, the MDMA measures a charge amount of the particle attached to the port in order to recognize the sizes or the distribution of the particles, but there is a problem in that the charge amount is not accurately measured in a case in which the charge amount of the particle is small, and as a result, it is impossible to measure the distribution of the particles, and particularly, it is impossible to accurately measure the number of particles to be classified.

As a method of measuring the number of particles, there is a method of condensing a liquid around the particle by using the particle as a condensation nucleus, growing the particle to make a large particle, and then optically counting the number of particles one by one. However, in the related art, a condensation nucleus counter (condensation particle counter (CPC)) is used by being connected to the MDMA or a particle classifier in order to measure the number of particles discharged from the MDMA or the particle classifier, and the particles discharged from the particle classifier pass through both a saturator and a condenser that constitute the condensation nucleus counter, and then the particles are measured as the particles reach a detector (or an optical device). In use of this configuration, the particles remain in the condensation nucleus counter over a very long period of time, and as a result, there is a problem in that a reaction time of the system is significantly increased.

In addition, the saturator and the condenser need to be separately configured for each size of the aerosol particle, and as a result, there is a problem in that a configuration of the system is complicated.

DISCLOSURE

Technical Problem

An aspect of the present invention provides an apparatus and a system for classifying particles which are efficient because the apparatus and the system may classify and capture aerosol particles according to the size even though a flow path for the aerosol is manufactured to have a short length, and may recognize the amount of generated particles, the sizes of the particles, and the distribution of the particles within a shorter period of time in comparison with the related art, thereby improving reliability in classifying the particles.

An aspect of the present invention also provides an apparatus and a system for classifying particles which may accurately measure the number of particles classified in the apparatus for classifying particles, simplify the configuration of the apparatus and the system, and recognize the number of particles (amount of generated particles), the sizes of the particles, and the distribution of the particles within a shorter period of time in comparison with the related art because a process in which classified particles pass through a saturating unit is omitted.

Technical Solution

According to an aspect of the present invention, there is provided an apparatus for classifying particles, the apparatus including: an internal electrode which has a column shape; an external electrode which is spaced apart from the internal electrode and disposed to surround the internal electrode, and generates an electric field through an interaction with the internal electrode; and an aerosol supply unit which supplies aerosol particles to a separation space between the internal electrode and the external electrode, in which the separation space, through which the aerosol particles are introduced into the particle classifying apparatus and flow, is formed to be narrowed toward a lower aerosol flow side from an upper aerosol flow side into which the aerosol particles are introduced.

The external electrode may be configured by a plurality of electrode rings stacked and connected in an up and down direction, and the aerosol particles may be discharged to the outside through a portion between the two adjacent electrode rings.

The electrode ring may include an electrode ring body which faces an inner surface of the internal electrode and forms the separation space, and a protruding portion which is connected to a lower end of the electrode ring body and protrudes radially outward.

A spacing protrusion, which allows the pair of adjacent electrode rings to be spaced apart from each other, may be provided on at least one of the electrode ring body and the protruding portion, and a slit may be formed between the pair of adjacent electrode rings by the spacing protrusion.

The apparatus may include an external housing which is provided on an outer circumferential portion of the external electrode and has an accommodating groove that accommodates the electrode ring.

A chamber, which allows the aerosol particles discharged from the separation space to remain in the chamber, may be formed between the electrode ring and the external housing, and the chamber may be a space formed between the electrode ring body, the protruding portion, and the accommodating groove.

At least one classified particle discharge hole, through which the aerosol particles are classified according to the size and discharged, may be formed in the external housing, the separation space and the chamber may be in communication with each other through the slit, and the chamber and the outside may be in communication with each other through the classified particle discharge hole.

The separation space may be formed to be narrowed from the upper aerosol flow side into which the aerosol particles are introduced toward the lower aerosol flow side from which the aerosol particles are discharged.

An air supply unit for supplying air to the separation space may have a cap structure coupled to cover one side of the separation space between the internal electrode and the external electrode, and has one or more air supply holes formed in a sidewall of the air supply unit, the aerosol supply unit may be coupled to penetrate the air supply unit, and an aerosol dispersing block for dispersing the aerosol particles may be further provided at an aerosol outlet side of the aerosol supply unit.

According to another aspect of the present invention, there is provided a system for classifying particles, the system including: a particle classifying apparatus which has an air supply unit for supplying air, and at least one classified particle discharge hole for classifying aerosol particles according to the size and discharging the aerosol particles; an air saturator which is connected to the particle classifying apparatus and saturates the air to make a saturated vapor; and at least one condenser which is provided separately from the air saturator and connected to the particle classifying apparatus or the air saturator, and condenses the aerosol particles included in the saturated vapor.

The number of air saturator may be one, and the number of condensers may be more than one so as to correspond to the number of classified particle discharge holes.

The system may further include detectors which are connected to the condensers, respectively, and detect the aerosol particles; and flow rate adjusters which adjust flow rates of the aerosol particles.

The system may further include a heater which is provided to surround the particle classifying apparatus and maintains a temperature of the particle classifying apparatus so that the temperature of the particle classifying apparatus is higher than or equal to a temperature of the air saturator.

The particle classifying apparatus may include: an internal electrode which has a column shape; an external electrode which is spaced apart from the internal electrode and disposed to surround the internal electrode, and generates an electric field through an interaction with the internal electrode; and an aerosol supply unit which supplies the aerosol particles, and a separation space, through which the aerosol particles are introduced into the particle classifying apparatus and flow, may be formed to be narrowed toward a lower aerosol flow side from an upper aerosol flow side into which the aerosol particles are introduced.

The internal electrode may be formed such that an outer diameter of the internal electrode is increased stepwise or gradually increased toward the lower aerosol flow side.

Advantageous Effects

The apparatus and the system for classifying particles according to the present invention are efficient because the apparatus and the system may classify and capture aerosol particles according to the size even though a flow path for the aerosol is manufactured to have a short length, and may recognize the amount of generated particles, the sizes of the particles, and the distribution of the particles within a shorter period of time in comparison with the related art, thereby improving reliability in classifying the particles.

According to the particle classifying system according to the present invention, the air saturator and the condenser are separately configured, the air saturator is disposed in the air supply unit inserted into the particle classifying apparatus, and the plurality of condensers is provided to condense the aerosol particles classified and discharged from the particle classifying apparatus. As a result, it is possible to accurately measure the number of particles classified in the particle classifying apparatus, simplify the configuration of the apparatus and the system, and recognize the number of particles (amount of generated particles), the sizes of the particles, and the distribution of the particles within a shorter period of time in comparison with the related art because a process in which classified particles pass through a saturating unit is omitted.

BEST MODE

Hereinafter, a first exemplary embodiment of a particle classifying system according to the present invention will be described in detail with reference to the accompanying drawings.

Figure 1:
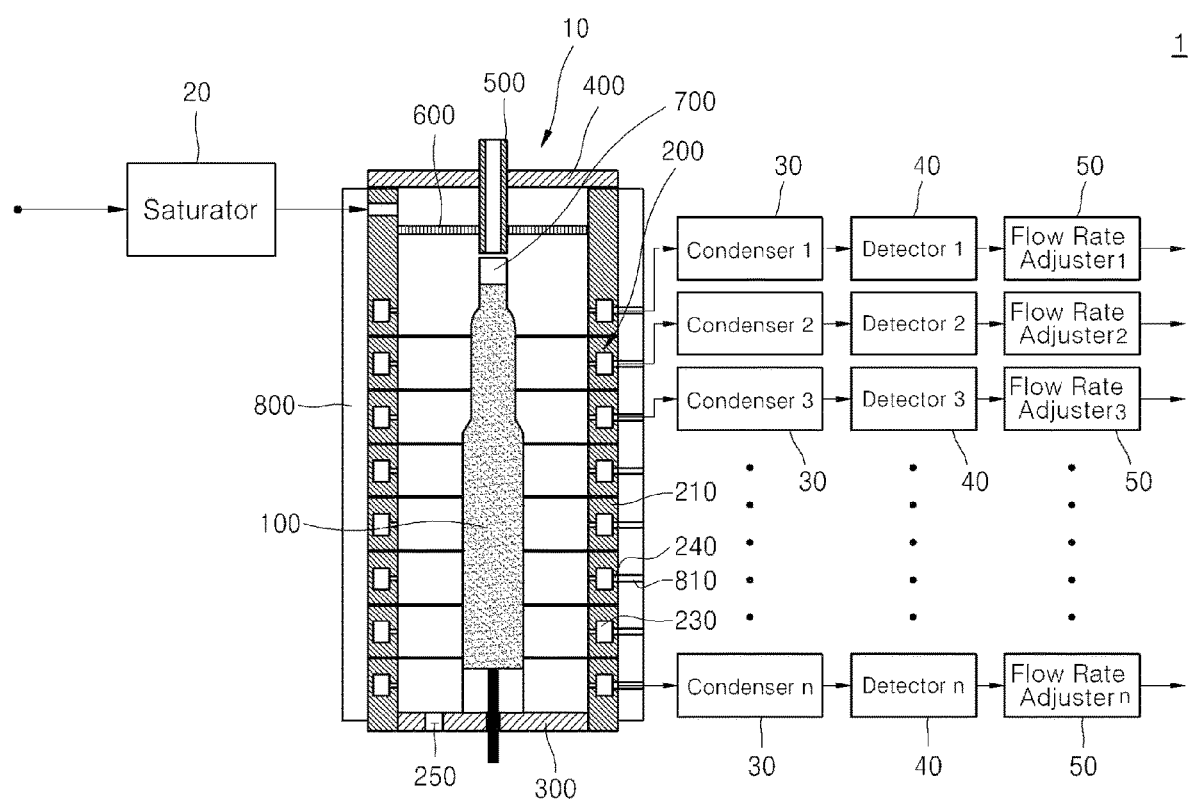
FIG. 1 is a view schematically illustrating a particle classifying system according to an exemplary embodiment of the present invention.
Figure 2:
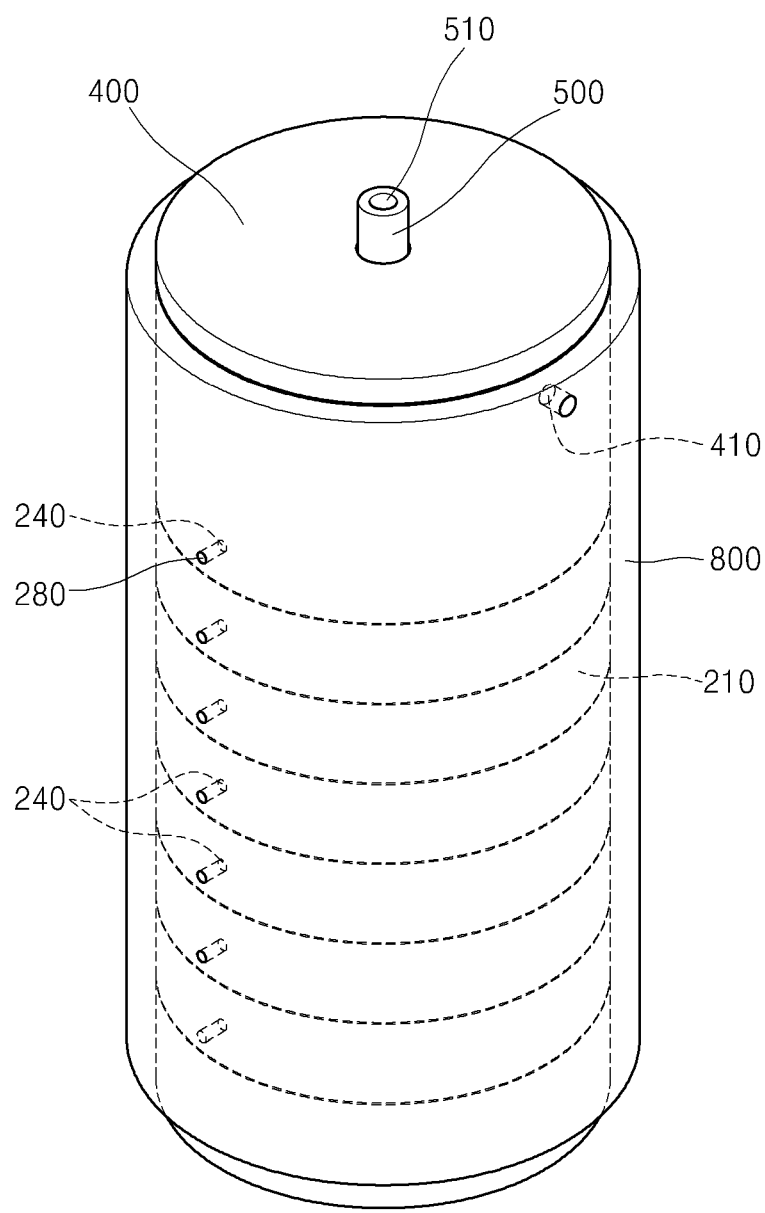
FIG. 2 is a perspective view of a particle classifying apparatus of the particle classifying system according to the exemplary embodiment of the present invention.
Figure 3:
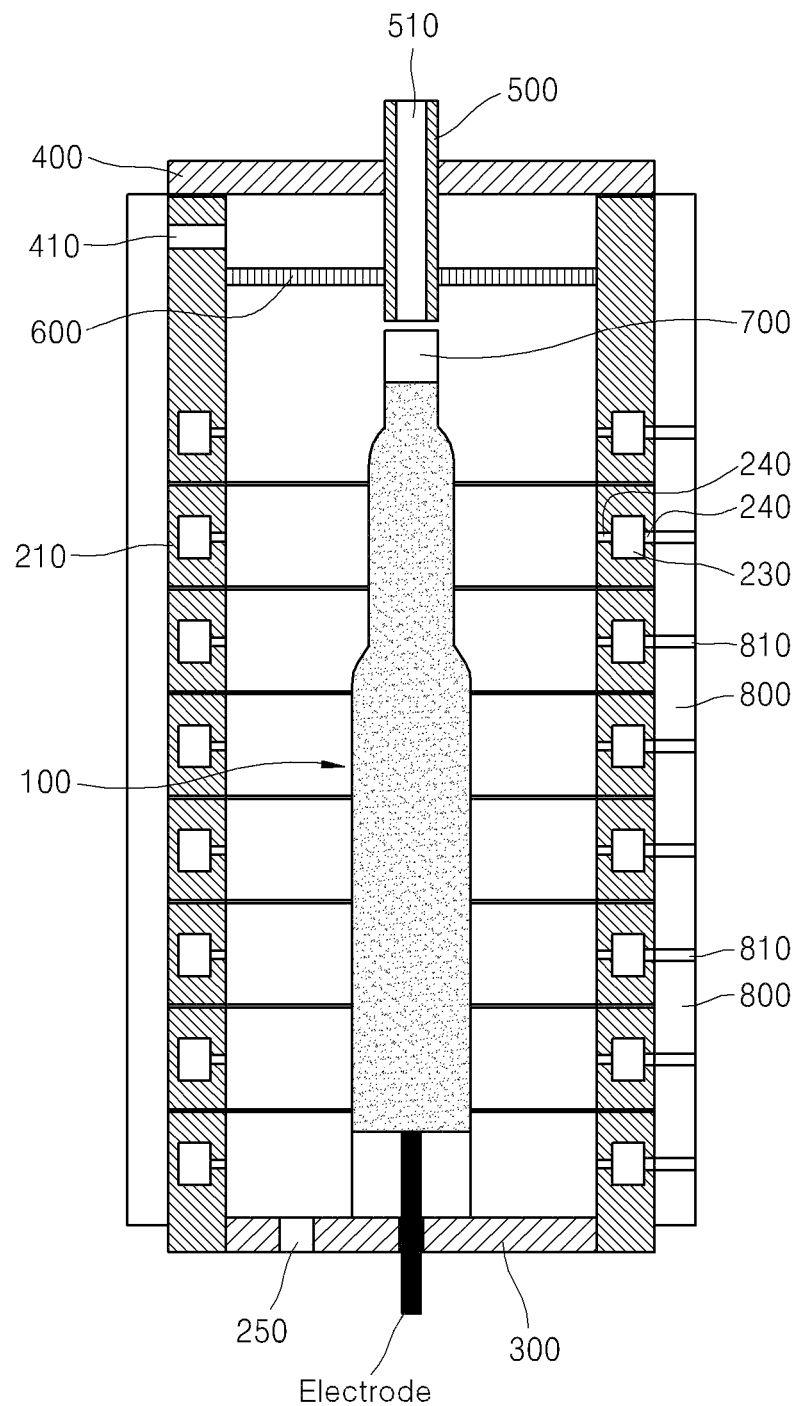
FIG. 3 is an assembled cross-sectional view of the particle classifying apparatus according to the exemplary embodiment of the present invention.
Figure 4A:
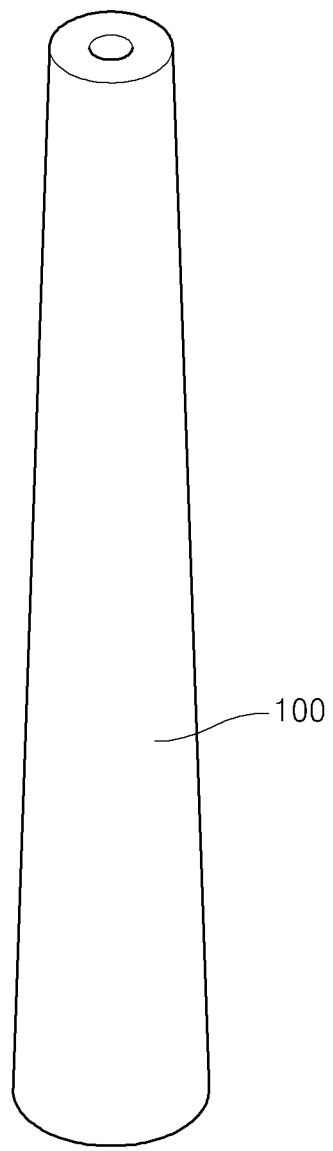
FIGS. 4a and 4b are perspective views of an internal electrode of the particle classifying apparatus according to the exemplary embodiment of the present invention.
Figure 4B:
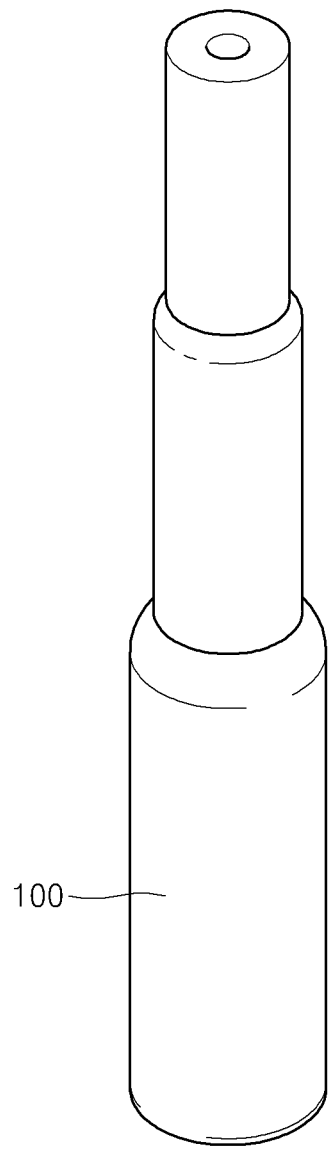

FIG. 1 is a view schematically illustrating a particle classifying system according to an exemplary embodiment of the present invention, FIG. 2 is a perspective view of an particle classifying apparatus of the particle classifying system according to the exemplary embodiment of the present invention, FIG. 3 is an assembled cross-sectional view of the particle classifying apparatus according to the exemplary embodiment of the present invention, and FIGS. 4a and 4b are perspective views of an internal electrode of the particle classifying apparatus according to the exemplary embodiment of the present invention.

A particle classifying system 1 according to an exemplary embodiment of the present invention is the particle classifying system 1 which uses a phenomenon in which when an electric field is applied to a space in which aerosol particles flow, the particles are moved toward one side by force caused by the electric field. The particle classifying system 1 is configured to classify the particles according to the size, accurately measure the number of particles, and have a higher response property than that in the related art.

To this end, as illustrated in FIG. 1, the particle classifying system 1 according to the exemplary embodiment of the present invention may include a particle classifying apparatus 10 which classifies aerosol particles according to the size by an electric field, an air saturator 20 which is connected to an air supply unit 400 of the particle classifying apparatus 10 and saturates the air to make a saturated vapor, and at least one condenser 30 which is provided separately from the air saturator 20 and condenses the aerosol particles included in the saturated vapor.

Here, the air saturator 20 may be connected to the particle classifying apparatus 10, and may be provided between the particle classifying apparatus 10 and the condenser 30. That is, the condenser 30 may be connected to the particle classifying apparatus 10 or the air saturator 20.

The particle classifying apparatus 10 is a part for substantially classifying aerosol particles or nanoparticles according to the size. Therefore, as illustrated in FIGS. 2 to 5, the particle classifying apparatus 10 may include a column-shaped internal electrode 100, an external electrode 200 which surrounds the internal electrode 100 and is spaced apart from the internal electrode 100, and an aerosol supply unit 500 and the air supply unit 400 which supply aerosol and air, respectively, into a space in which the internal electrode 100 and the external electrode 200 are spaced apart from each other (hereinafter, referred to as a 'separation space').

The internal electrode 100 is a part for forming an electric field through an interaction with the external electrode 200, and the internal electrode 100 may have a column shape. The internal electrode 100 illustrated in FIG. 4*a* may be formed to be tapered so that an outer diameter of the internal electrode 100 is gradually increased from an upper aerosol flow side to a lower aerosol flow side. In contrast, the internal electrode 100 illustrated in FIG. 4*b* is formed to be stepped and thus have a stepped shape so that an outer diameter of the internal electrode 100 is increased stepwise toward the lower aerosol flow side. The shape of the internal electrode 100 may vary in consideration of a structure by which the electric field is efficiently applied to the aerosol particles, an arrangement relationship in the separation space, or the like.

Meanwhile, in the exemplary embodiment of the present invention illustrated in FIG. 3, the internal electrode 100, which is formed to be stepped to have stepped portions, is used as the internal electrode 100.

Mainly referring to FIGS. 1 to 3, the external electrode 200 is provided to surround an outer circumferential portion of the internal electrode 100. In addition, the external electrode 200 accommodates therein the internal electrode 100, and may be disposed to be spaced apart from the internal electrode 100 so as to form the separation space in which the aerosol particles are classified while flowing. The external electrode 200 may be configured by an electrode ring 210 having a ring shape, and as illustrated in FIG. 3, the external electrode 200 may include a plurality of electrode rings 210 which is stacked and coupled in an up and down direction, in a flow direction of the aerosol particles.

Further, mainly referring to FIG. 3, the electrode rings 210, which are adjacent to each other in the up and down direction, are disposed to be in close contact with each other, thereby isolating the separation space in the particle classifying apparatus 10 from the outside. A classified particle discharge hole 240 is provided in each of the electrode rings 210, and the classified particle discharge hole 240 serves to discharge the captured particles to the outside of the external electrode 200. The plurality of classified particle discharge holes 240 is provided around the electrode rings 210, such that the aerosol particles may be discharged while being spread in all directions, and as a result, the single classified particle discharge hole 240 may be provided in the single electrode ring 210.

According to the internal electrode 100 and the external electrode 200, a size of the separation space or a separation distance (distance between an outer diameter of the internal electrode 100 and an inner diameter of the external electrode 200) varies from the upper aerosol flow side to the lower side, such that the aerosol particles having different sizes may be classified.

The separation space between the internal electrode 100 and the external electrode 200 according to the exemplary embodiment of the present invention is formed to be narrowed from the upper aerosol flow side, at which the aerosol particles are introduced, to the lower aerosol flow side at which the aerosol particles are discharged. Further, the separation space is configured such that the aerosol particles having larger sizes are classified at the lower aerosol flow side.

That is, the external electrode 200 has a constant inner diameter, but the internal electrode 100 is formed so that an outer diameter of the internal electrode 100 is increased gradually or stepwise from the upper aerosol flow side to the lower side, and as a result, the separation space between the external electrode 200 and the internal electrode 100 is narrowed toward the lower aerosol flow side. A stronger electric field is formed in the separation space as the internal electrode 100 becomes closer to the external electrode 200, such that even the particle having a large diameter may be quickly moved to the external electrode 200 and captured.

A process in which the aerosol particles are moved by using the electric field formed between the internal electrode 100 and the external electrode 200 will be described. The motion of the aerosol particles (charged particles) exposed between the two electrodes (the external electrode 200 and the internal electrode 100) may be expressed by the following Expression 1.

$$x = \frac{Q \cdot \ln(r_2/r_1)}{2\pi \cdot z_p \cdot V} = \frac{Q \cdot \ln(r_2/r_1)}{2 \cdot V} \frac{3\mu D_p}{q \cdot C_c} \quad \text{[Expression 1]}$$

(x: particle movement distance, Q: total flow rate, r1: outer diameter of internal electrode, r2: inner diameter of external electrode, μ: viscosity coefficient of gas, Dp: diameter of particle, V: applied voltage, q: charge amount of particle, Cc: Cunningham slip correction factor)

As expressed in Expression 1, the movement distance of the particle is proportional to the diameter of the particle, such that the particles having a relatively small diameter are captured first at an inlet side of a flow path, that is, at the upper aerosol flow side (upper side in the present exemplary embodiment), and the particles having a relatively large diameter are moved and then captured at a rear end of the flow path, that is, at the lower aerosol flow side (lower side in the present exemplary embodiment), and as a result, the particles may be classified and captured sequentially according to the size from the upper side to the lower side of the particle classifying apparatus 10. Because the technical spirit in which the particles flowing between the internal electrode 100 and the external electrode 200 are moved to the external electrode 200 by the electric field is also equally applied to the particle classifying apparatus 10 in the related art, a detailed description thereof will be omitted.

A stronger electric field is generated in the separation space as the internal electrode 100 becomes closer to the external electrode 200, such that even the particle having a large diameter may be quickly moved to the external electrode 200 and captured. It can be seen from Expression 1 that the movement distance of the particles is increased in accordance with the separation distance between the internal electrode 100 and the external electrode 200.

Therefore, the particles may be selected and classified according to the size while the particles flow from the upper aerosol flow side to the lower side, the particles may be classified and captured to the plurality of electrode rings 210, and the captured particles may be discharged to the classified particle discharge holes 240.

Meanwhile, a chamber 230 may be provided in the electrode ring 210 along a circumference of the electrode ring 210. Mainly referring to FIG. 3, the chamber 230 may be formed to have a space that has a quadrangular cross section and is shielded from the outside along the circumference of the electrode ring 210 so as to accommodate the particles. Further, the chamber 230 is not a space completely isolated from the outside, but the chamber 230 may be connected to the outside through the classified particle discharge hole 240. That is, the classified particle discharge hole 240 is in communication with a partial region of the chamber 230, such that the classified particle discharge hole 240 may connect the separation space in the particle classifying apparatus 10 to the outside of the external electrode 200. The chamber 230 is a kind of buffer space that serves to allow the particles discharged from the classified particle discharge hole 240 to remain in the chamber 230 for a moment so that the particles are widely spread in the space of the chamber 230 and the pressure is generally decreased uniformly overall, thereby preventing a pressure of a flow from being locally non-uniform only at the classified particle discharge hole 240. Here, the chamber 230 may have various shapes in addition to the shape having the quadrangular cross section.

Mainly referring to FIGS. 2 and 3, the air supply unit 400 may be provided at the upper side of the particle classifying apparatus 10. The air supply unit 400 has a cap structure coupled to cover an upper side of the separation space between the internal electrode 100 and the external electrode 200, and may have an air supply hole 410 formed in a sidewall of the air supply unit 400. Further, the air saturator 20 may be provided between the outside air and the air supply unit 400. The air saturator 20 will be described below.

The aerosol supply unit 500 may be provided at a central portion of the air supply unit 400. The aerosol supply unit 500 may be coupled to penetrate the air supply unit 400 and may be configured to be in communication with an interior of an upper side of the particle classifying apparatus 10. Both the air and the aerosol particles to be classified may be supplied to the interior of the upper side of the particle classifying apparatus 10 through the air supply unit 400 and the aerosol supply unit 500.

In this case, the aerosol particles and the air need to be uniformly supplied over the entire separation space, and first, an aerosol dispersing block 700 may be additionally provided at an outlet side of the aerosol supply unit 500, that is, at a lower end of the aerosol supply hole 510 in the present exemplary embodiment in order to uniformly supply the aerosol particles to the separation space in all directions. The aerosol passing through the outlet of the aerosol supply unit 500 collides with an upper surface of the aerosol dispersing block 700 and is dispersed in all directions, such that the aerosol may be uniformly delivered to the entire separation space.

In addition, an air filter 600 may be provided at a part of an inner region of the air supply unit 400. The air filter 600 may be provided at the lower aerosol flow side relative to the air supply hole 410 and may be provided at the upper side relative to the aerosol supply unit 500, such that the air introduced into the air supply hole 410 may flow to the lower aerosol flow side while being filtered by the air filter 600. Since the air is filtered by the air filter 600 and then supplied to the separation space, it is possible to prevent the flow and the capture of the particles from being hindered by dust or foreign substances. In addition, because the air filter 600 has a lattice structure or a web structure formed in one direction, the air filter 600 forms a laminar flow while the air passes through the air filter 600, and the air uniformly passes through the entire air filter 600, such that the air is more uniformly supplied to the separation space. The air passing through the air filter 600 is mixed with the aerosol particles spread in all directions by the aerosol dispersing block 700 and then flows to the lower aerosol flow side.

The aerosol supply unit 500 remains electrically conducted with the external electrode 200*a*, and in this state, the charged particles are introduced through the aerosol supply hole 510. If the aerosol dispersing block 700 is a conductor, the charged particles may be attached to the aerosol dispersing block 700. Therefore, an insulator (not illustrated) needs to be inserted between the aerosol dispersing block 700 and the internal electrode 100 in order to electrically insulate the internal electrode 100 and the aerosol dispersing block 700, such that a loss of the particles may be reduced and the particles may be more accurately measured.

To this end, an insulator (not illustrated) may be provided between the aerosol dispersing block 700 and the internal electrode 100 according to the present invention particle classifying apparatus.

A base 300 may be provided at the lower aerosol flow side of the particle classifying apparatus 10. The base 300 isolates the separation space of the particle classifying apparatus 10 from the outside, and a remaining particle discharge hole 250, through which the aerosol particles, which are not captured, may be discharged, may be formed in a partial region of the base 300.

Meanwhile, the MDMA in the related art may classify the particles according to the size, but cannot accurately measure the number of particles. Further, in a case in which an optical counting method is used to measure the number of aerosol particles, a saturating unit and a condensing unit need to be configured for each size of the aerosol particle to be classified, and as a result, there is a problem in that a relatively long period of time is required for the aerosol particles, which are classified according to the size while passing through the particle classifying apparatus, to individually pass through the saturating unit and the condensing unit, and as a result, a long period of time is required to recognize the sizes and the distribution of the particles.

To solve the aforementioned problem, in the present invention, the air saturator 20 and the condenser 30 are separately configured, the air saturator 20 is disposed on the air supply unit 400 inserted into the particle classifying apparatus 10, and the plurality of condensers 30, which condenses the aerosol particles classified and discharged from the particle classifying apparatus 10, may be provided to correspond to the number of aerosol particles to be classified.

To this end, the particle classifying system 1 according to the exemplary embodiment of the present invention may include the at least one air saturator 20 which is connected to the air supply unit 400, and the plurality of condensers 30 which is connected to the classified particle discharge holes 240 through which the classified aerosol particles are discharged. The air saturator 20 may be provided to be connected to the air supply unit 400. The air saturator 20 is a part that receives outside air (clean sheath air) and saturates the air to make a vapor, and accommodates a working fluid such as water, alcohol, and ethylene glycol. The working fluid accommodated in the air saturator 20 is heated and vaporized, and the outside air introduced into the air saturator 20 is converted into a saturated vapor by the vaporized working fluid.

The saturated vapor introduced into the particle classifying apparatus 10 is mixed with the aerosol particles and forms a laminar flow while passing through the air filter 600, and the saturated vapor flows to the lower side of the particle classifying apparatus 10, that is, to the lower aerosol flow side.

The saturated vapor, which includes the particles flowing in the particle classifying apparatus 10, may be condensed at any time when a temperature is decreased, and as a result, it is necessary to prevent the saturated vapor from being condensed during the process in which the particles are classified in the particle classifying apparatus 10. To this end, a heater 800 may be provided to surround the particle classifying apparatus 10. With the heater 800, it is possible to maintain a temperature of the particle classifying apparatus 10 which is equal to or higher than a temperature of the air saturator 20, thereby preventing a problem in that the saturated vapor is condensed in the separation space of the particle classifying apparatus 10 and the particles cannot be classified. Meanwhile, the heater 800 may have a plurality of connecting holes 810 which is in communication with the classified particle discharge holes 240.

The saturated vapor including the particles is classified by the electric field in the particle classifying apparatus 10 and captured by the respective electrode rings 210 as described above, and the saturated vapor may be discharged to the outside via the classified particle discharge holes 240. Mainly referring to FIG. 1, the respective condensers 30 are connected to the respective classified particle discharge holes 240. Further, the particle classifying apparatus 10 may further include detectors 40 which are connected to the respective condensers 30 and detect the aerosol particles, and flow rate adjusters 50 which adjust a flow rate of the aerosol particles. With this configuration, the condenser 30 condenses the saturated vapor including the aerosol particles discharged from the particle classifying apparatus 10. The particles, which are grown by the condensation of the saturated vapor, are detected in an optical manner or other manners by the detectors 40 connected to the condensers 30, as a result, it is possible to accurately count the number of particles.

In the exemplary embodiment of the present invention, the single air saturator 20 may be provided to be connected to the air supply unit 400, and the plurality of condensers 30, the plurality of detectors 40, and the plurality of flow rate adjusters 50 may be provided to correspond to the number of classified particle discharge holes 240.

With the configurations of the air saturator 20, the particle classifying apparatus 10, and the condensers 30, it is possible to more accurately measure the number of particles classified in the particle classifying apparatus 10 in comparison with the related art.

In addition, a reaction property of the particle classifying apparatus 10 may reduce the time in comparison with the existing equipment. That is, a process of using several saturators for the classified aerosol particles in the existing apparatus is omitted, and the single air saturator 20 is used, such that it is possible to very quickly and accurately measure the number, the sizes, and the distribution of the particles, and the configuration of the apparatus may be relatively simplified in comparison with the case in which several saturators are used.

Figure 5:
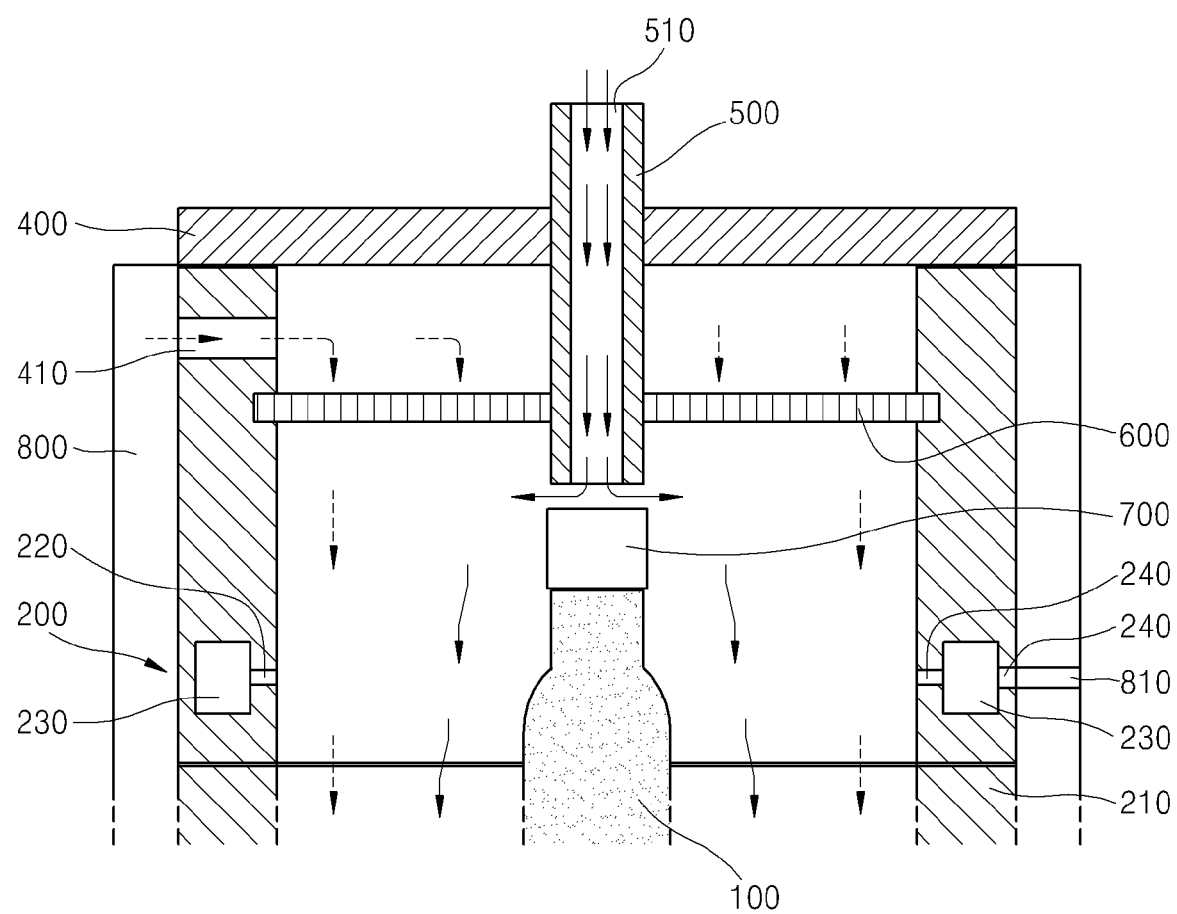
FIGS. 5 and 6 are enlarged cross-sectional views of the particle classifying apparatus according to the exemplary embodiment of the present invention.
Figure 6:
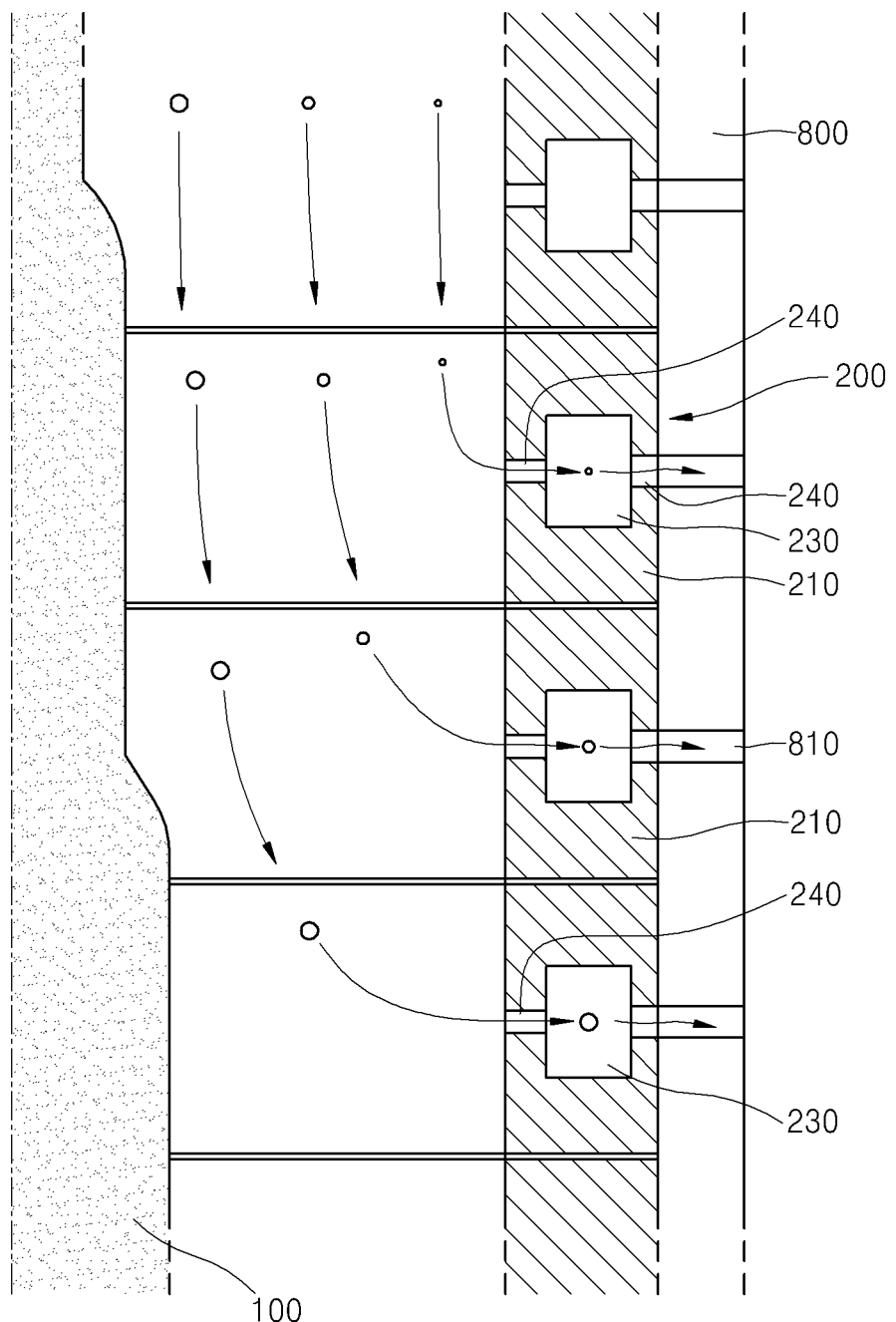

FIGS. 5 and 6 are enlarged cross-sectional views of the particle classifying apparatus according to the exemplary embodiment of the present invention. The process in which the particles having different sizes are moved to the external electrode 200 and classified according to the size and then captured and the analysis process will be described in detail with reference to FIGS. 5 and 6.

First, outside air is converted into a saturated vapor while passing through the air saturator 20, and the saturated vapor is introduced into the particle classifying apparatus 10. In addition, aerosol particles are introduced into the upper side of the particle classifying apparatus 10 from the aerosol supply unit 500, and in this case, the aerosol particles are introduced while being uniformly spread in all directions by the aerosol dispersing block 700. The introduced aerosol particles are mixed with the saturated vapor while being spread and flow to the lower aerosol flow side, and the aerosol particles flow by being converted into a laminar flow while passing through the air filter 600.

The particles flowing along the separation space are classified according to the size, and discharged to the outside through the classified particle discharge holes 240 formed in the respective electrode rings 210 that constitute the external electrode 200. In this process, the pressure is uniformly decreased by the chamber 230, and the particles flow to the condenser 30.

Thereafter, the respective condensers 30 connected to the respective classified particle discharge holes 240 may be provided to condense the saturated vapor in order to optically count the number of particles, and as a result, it is possible to accurately measure the number of classified particles within a shorter period of time in comparison with the related art.

Meanwhile, the present exemplary embodiment discloses only the case in which the inner diameter of the external electrode 200 remains constant in the up and down direction, and the outer diameter of the internal electrode 100 is increased toward the lower aerosol flow side, such that the interval between the internal electrode 100 and the external electrode 200 is decreased. However, the outer diameter of the internal electrode 100 may remain constant in the up and down direction, and the inner diameter of the external electrode 200 may be decreased toward the lower aerosol flow side, such that the interval between the internal electrode 100 and the external electrode 200 is decreased. Because the effect of more easily capturing the particles having a large diameter may be equally implemented even in the case in which the interval between the internal electrode 100 and the external electrode 200 is decreased as the inner diameter of the external electrode 200 is decreased toward the lower side as described above, a detailed description thereof will be omitted.

In addition, the present exemplary embodiment discloses only the structure in which the internal electrode 100 and the external electrode 200 are vertically placed, but the particle classifying system 1 according to the present invention may be configured to be disposed horizontally or inclined diagonally.

Figure 7:
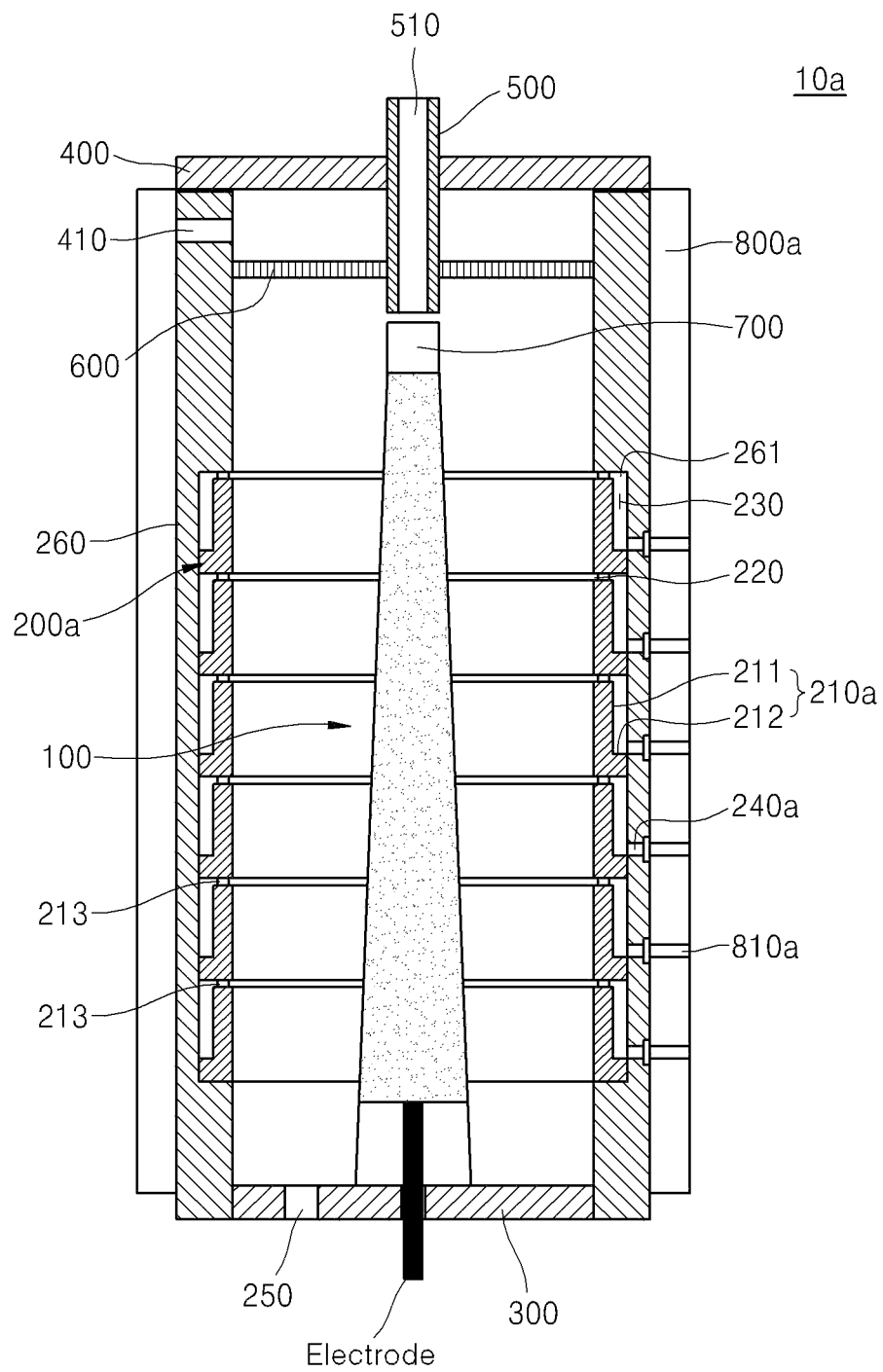
FIG. 7 is an assembled cross-sectional view of a modified example of the particle classifying apparatus applied to the particle classifying system according to the exemplary embodiment of the present invention.
Figure 8:
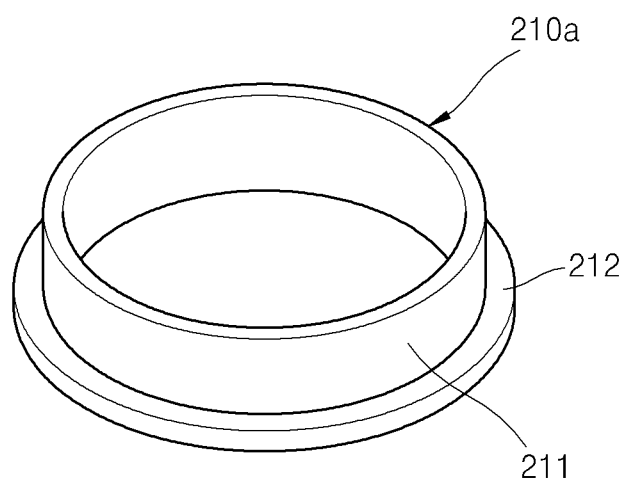
FIG. 8 is a perspective view of an external electrode applied to the particle classifying apparatus illustrated in FIG. 7.
Figure 9:
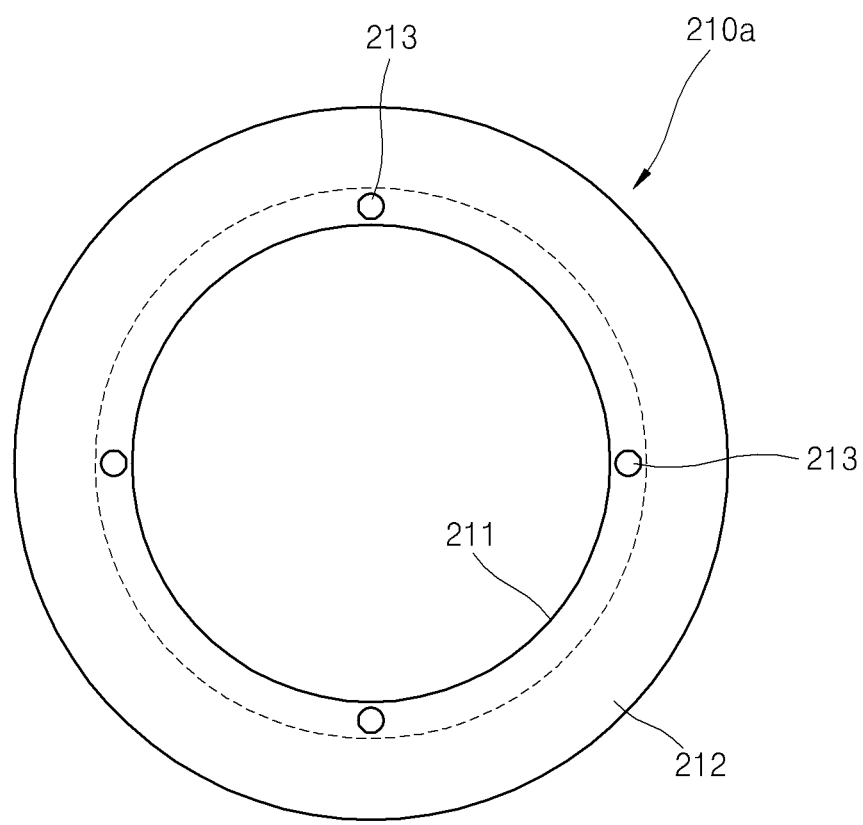
FIG. 9 is a bottom plan view of the external electrode illustrated in FIG. 8.
Figure 10:
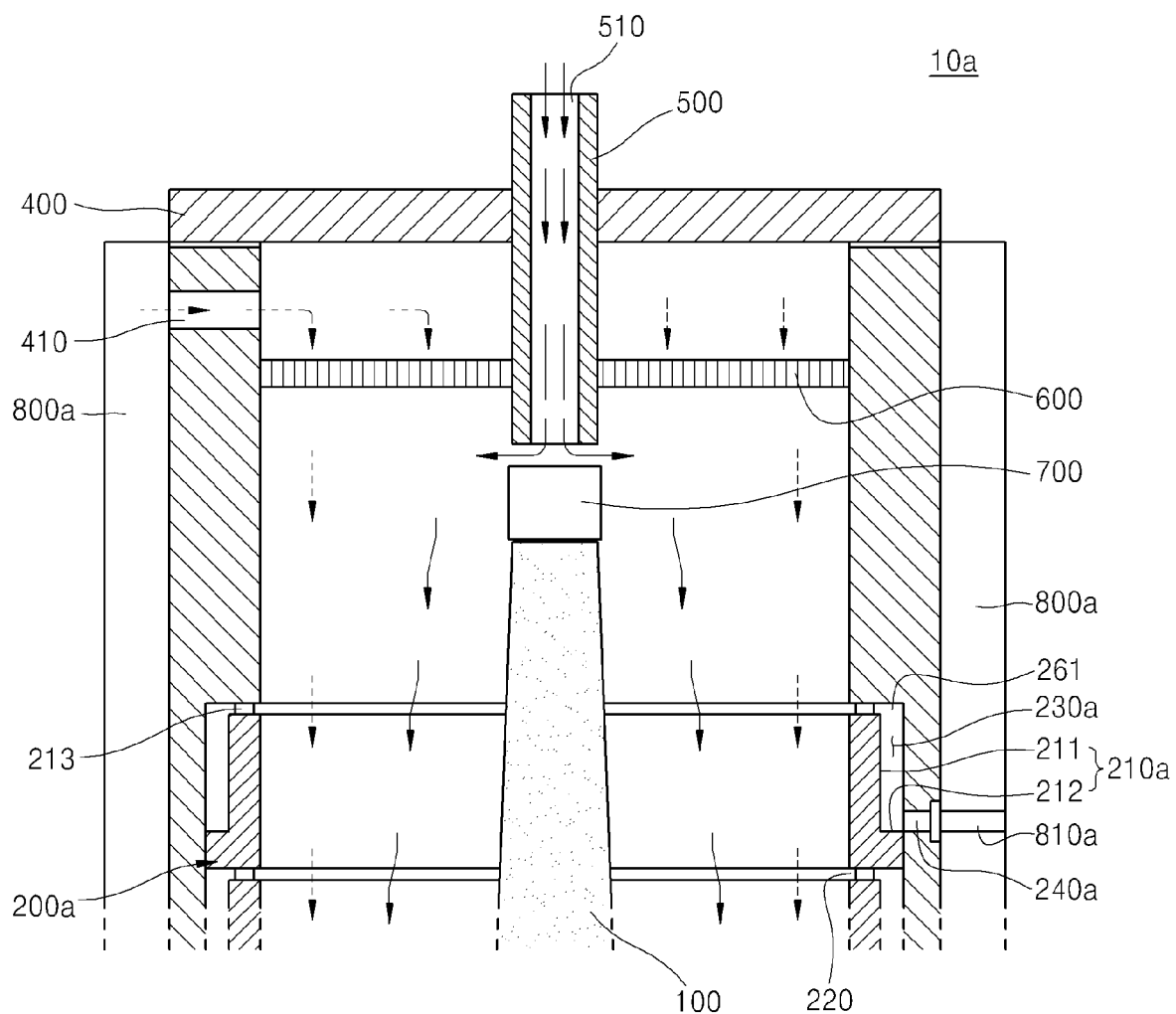
FIGS. 10 and 11 are enlarged cross-sectional views of the particle classifying apparatus illustrated in FIG. 7.
Figure 11:
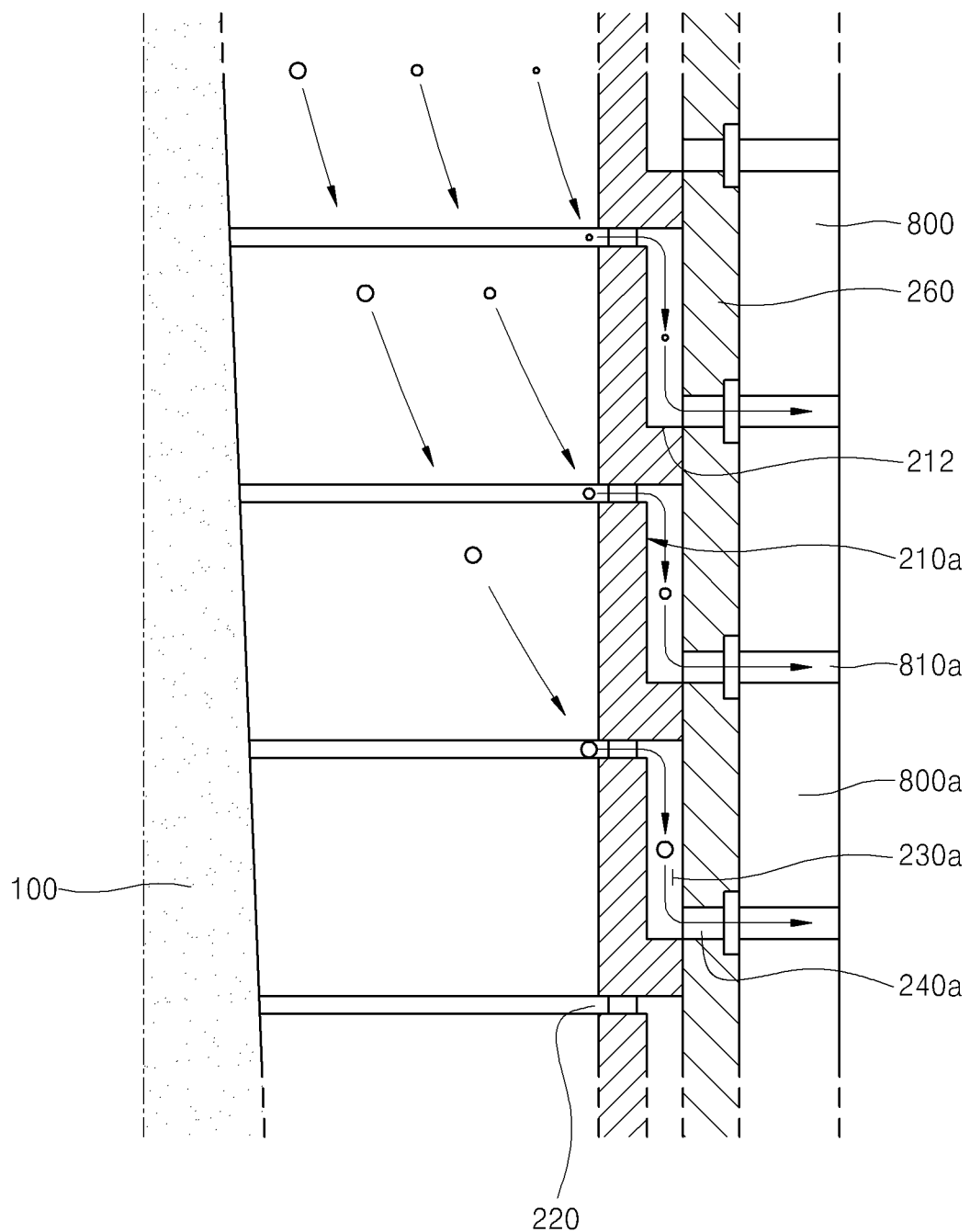

FIG. 7 is an assembled cross-sectional view of a modified example of the particle classifying apparatus applied to the particle classifying system according to the exemplary embodiment of the present invention, FIG. 8 is a perspective view of the external electrode applied to the particle classifying apparatus illustrated in FIG. 7, FIG. 9 is a bottom plan view of the external electrode illustrated in FIG. 8, and FIG. 10 and FIG. 11 are enlarged cross-sectional views of the particle classifying apparatus illustrated in FIG. 7.

A particle classifying apparatus 10a illustrated in FIG. 7 differs from the particle classifying apparatus 10 illustrated in FIGS. 1 to 6 in terms of a shape and a configuration of an external electrode 200a, and an external housing 260 for accommodating the external electrode 200a may be additionally provided. In addition, there are also differences in terms of positions of classified particle discharge holes 240a and an arrangement relationship of chambers 230a, and hereinafter, only the differentiated configurations will be described.

As illustrated in FIGS. 7 to 9, in the present exemplary embodiment, the external electrode 200a of the particle classifying apparatus 10a includes a plurality of electrode rings 210a which is stacked and connected in the up and down direction, each of the electrode rings 210a has a protruding portion 212, and the external housing 260 may be additionally provided outside the electrode rings 210a.

That is, each of the electrode rings 210a of the external electrode 200a may include an electrode ring body 211 which is formed around a circumference, and the protruding portion 212 which is bent and protrudes in a radial direction from a lower end of the electrode ring body 211.

The electrode ring body 211 may be provided along the circumference so as to be spaced apart from the internal electrode 100 at a predetermined interval in order to form the separation space, and the protruding portion 212 is a portion that is bent and protrudes radially and outward from a lower end portion of the electrode ring body 211, and may serve to form the chamber 230a to be described below.

A spacing protrusion 213 may be provided on a bottom surface of the protruding portion 212. The spacing protrusion 213 serves to form a slit 220 between the two adjacent electrode rings 210a when the electrode rings 210a are stacked. The plurality of spacing protrusions 213 may be provided to be spaced apart from one another at a predetermined angle along the circumference. Meanwhile, the present exemplary embodiment discloses the configuration in which the spacing protrusion 213 is provided on the bottom surface of the protruding portion 212, but the spacing protrusion 213 may be provided on an upper surface of the electrode ring body 211.

Since the slit 220 is formed between the electrode rings 210a by the spacing protrusion 213, it is not necessary to form a separate through hole in the electrode ring 210a in order to discharge the particles. That is, the slits 220, which allow the particles to be easily discharged, may be formed by the spacing protrusions 213 only by stacking the plurality of electrode rings 210a in the up and down direction. Therefore, it is not necessary to penetrate the sidewall of the electrode ring, such that a process of manufacturing the external electrode 200a is simplified. In a case in which any one part of the electrode ring 210a is fractured or damaged, only the corresponding electrode ring 210a may be replaced or reused after repair, such that costs required to repair and maintain the external electrode 220a are reduced. The classified aerosol particles may be discharged through the slits 220. That is, the aerosol particles flowing in the separation space or the captured particles may be discharged to the outside through the space formed between the two adjacent electrode rings 210a. That is, the two electrode rings 210a, which are adjacent to each other in the up and down direction, are not in close contact with each other, but stacked to be spaced apart from each other at a predetermined interval to form the slit 220.

Here, the spacing protrusion 213 may be formed on the bottom surface of the protruding portion 212 or formed on the upper end surface of the electrode ring body 211.

The external housing 260 may be provided on an outer circumferential portion of the external electrode 210a so as to be disposed to surround the external electrode 210a. The external housing 260 has an accommodating groove 261 formed along an inner wall of the external housing 260, and the plurality of stacked electrode rings 210a may be accommodated in the accommodating groove 261. The external housing 260 is a member capable of maintaining the stacked state of the plurality of electrode rings 210a stacked in the up and down direction. That is, since the plurality of stacked electrode rings 210a is accommodated in the accommodating groove 261 of the external housing 260, it is possible to maintain the stacked state of the plurality of electrode rings 210a without a separate fixing means.

The plurality of classified particle discharge holes 240a may be formed in the external housing 260 in a direction from the upper aerosol flow side to the lower side, that is, in the up and down direction. The classified particle discharge holes 240a may be connected to the electrode rings 210a disposed to correspond to heights of the classified particle discharge holes 240a. In a case in which the classified particle discharge holes 240a are provided around the circumference of the external housing 260, the aerosol particles are discharged while being spread in all directions, and as a result, it may be difficult to perform processes after capturing the particles (i.e., processes of measuring and analyzing the distribution or the sizes of the particles). Therefore, one classified particle discharge hole 240*a* may be provided to correspond to one electrode ring 210*a*.

The chamber 230*a* may be a predetermined space formed by the protruding portion 212 of the electrode ring 210*a* and the external housing 260, and the chamber 230*a* may serve to allow the aerosol particles, which are discharged while passing through the slit 220, to remain for a predetermined period of time so that the pressure is uniformly decreased.

In other words, the chamber 230*a* may be formed in a partial region of the accommodating groove 261 of the external housing 260. That is, the chamber 230*a* is a space formed between the electrode ring body 211, the protruding portion 212, and the accommodating groove 261. The chamber 230*a* serves to allow the particles discharged from the slit 220 to remain in the chamber 230*a* for a moment so that the particles are widely spread in the chamber 230*a* (formed in the circumferential direction) and the pressure is generally decreased uniformly overall, thereby preventing a pressure of a flow from being locally non-uniform only at the classified particle discharge hole 240*a*. The chamber 230*a* may refer to a kind of buffer space.

The separation space and the chamber 230*a* may be in communication with each other through the slit 220, and the chamber 230*a* and a line of the condenser (not illustrated) may be in communication with each other through the classified particle discharge hole 240*a*. That is, the aerosol particles flowing along the separation space may be classified and captured by the external electrode 210*a*, the aerosol particles may be introduced into the chambers 230*a* through the slits 220, and then the aerosol particles may be discharged to the condensers through the classified particle discharge holes 240 formed in the external housing 260.

Meanwhile, a saturated vapor or a working fluid may flow together with the aerosol particles in order to assist the flow of the aerosol particles flowing in the particle classifying apparatus 10*a*. The configuration in which the saturated vapor is introduced into the particle classifying apparatus 10*a* may be implemented by adding a configuration such as an air saturator (not illustrated) or providing a system including an air saturator and a condenser (not illustrated). Because the aerosol particles with the accompanying saturated vapor may be condensed when a temperature is decreased in the particle classifying apparatus 10*a*, it is necessary to prevent the condensation during the process of classifying the particles in the particle classifying apparatus 10*a*. To this end, a heater 800*a* may be provided to surround an outer surface of the external housing 260 of the particle classifying apparatus 10*a*. The heater 800*a* may serve to maintain the temperature in the particle classifying apparatus 10*a*. A plurality of connecting holes 810*a*, which is in communication with the classified particle discharge holes 230*a* of the external housing 260, may be provided in the heater 800*a*.

FIGS. 10 and 11 are enlarged cross-sectional views of the particle classifying apparatus illustrated in FIG. 7. The process in which the aerosol particles having different sizes are moved to the external electrode 200*a* and classified according to the size and then captured will be described in detail below with reference to FIGS. 10 and 11.

First, outside air is introduced into the particle classifying apparatus 10*a*. In addition, aerosol particles are introduced into the upper side of the particle classifying apparatus 10*a* from the aerosol supply unit 500, and in this case, the aerosol particles are introduced while being uniformly spread in all directions by the aerosol dispersing block 700. The introduced aerosol particles are mixed with air while being spread and flow to the lower aerosol flow side, and the aerosol particles flow by being converted into a laminar flow while passing through the air filter 600.

The aerosol particles flowing along the separation space are classified according to the size while flowing to the lower aerosol flow side, and may be captured by the respective electrode rings 210*a*. That is, the internal electrode 100 has a configuration in which the outer diameter of the internal electrode 100 is increased toward the lower aerosol flow side, and the separation space between the internal electrode 100 and the external electrode 200*a* is gradually narrowed, and as a result, the aerosol particles may be captured according to the size by the corresponding electrode rings 210*a*. Therefore, even the particles having a large diameter may be captured without ensuring a long length of the flow path through which the aerosol particles flow (a length of the separation space in the up and down direction), and as a result, it is possible to reduce a size of the apparatus, ensure efficiency of the apparatus, and reduce the time required to classify and capture the particles according to the size because the flow path of the particles is shortened.

Thereafter, the particles may be introduced into the chamber 230*a* through the slit 220. In this case, the chamber 230*a* allows the particles discharged from the slit 220 to be widely spread in the space of the chamber 230*a* while remaining in the chamber 230*a* for a moment so that the pressure is generally decreased uniformly overall.

The classified aerosol particles are discharged to the outside through the classified particle discharge holes 240*a* of the external housing 260 and the connecting holes 810*a* of the heater 800*a*.

Thereafter, the configurations such as the condenser or the detector (not illustrated) or the flow rate adjuster (not illustrated) may be added in order to accurately measure the number, the sizes, or the distribution of the classified aerosol particles.

Meanwhile, the present exemplary embodiment discloses only the case in which the inner diameter of the external electrode 200*a* remains constant in the up and down direction, and the outer diameter of the internal electrode 100 is increased toward the lower aerosol flow side, such that the interval between the internal electrode 100 and the external electrode 200*a* is decreased. However, the outer diameter of the internal electrode 100 may remain constant in the up and down direction, and the inner diameter of the external electrode 200*a* may be decreased toward the lower aerosol flow side, such that the interval between the internal electrode 100 and the external electrode 200*a* is decreased. Because the effect of more easily capturing the particles having a large diameter may be equally implemented even in the case in which the interval between the internal electrode 100 and the external electrode 200*a* is decreased as the inner diameter of the external electrode 200*a* is decreased toward the lower side as described above, a detailed description thereof will be omitted.

In addition, the exemplary embodiment of the present invention discloses only the structure in which the internal electrode 100 and the external electrode 200a are vertically placed, but the particle classifying apparatus 10a according to the present invention may be configured to be disposed horizontally or inclined diagonally.

In addition, the particle classifying system including the particle classifying apparatus 10a is identical to the exemplary embodiment illustrated in FIG. 1 in terms of the process in which the saturated vapor is introduced into the particle classifying apparatus 10 by the air saturator 20 and the aerosol particles are introduced. The particles flowing along the separation space are classified according to the size, captured by the respective electrode rings 210a that constitute the external electrode 200a, and then discharged to the outside while passing through the chambers 230a and the classified particle discharge holes 240a through the slits 220 formed between the electrode rings. Thereafter, the number of classified aerosol particles discharged from the respective classified particle discharge holes 240a is counted, such that the number, the sizes, and the distribution of the particles may be accurately measured, and these configurations are identical to those described above.

While the exemplary embodiments of the present invention have been described in detail above, the scope of the present invention is not limited to the exemplary embodiments, and the scope of the present invention should be defined by the appended claims. Furthermore, it should be noted that those skilled in the art may variously modify and change the exemplary embodiments without departing from the scope of the present invention.

INDUSTRIAL APPLICABILITY

The present invention may be used in the field of environment measurement, the field for measuring nanoparticles in real time, or the field for measuring concentration, sizes, and distribution of soot and smoke from diesel engines.

The invention claimed is:

1. An apparatus for classifying particles, the apparatus comprising:
    an internal electrode which has a column shape;
    an external electrode which is spaced apart from the internal electrode and disposed to surround the internal electrode, and generates an electric field through an interaction with the internal electrode; and
    an aerosol supply unit which supplies aerosol particles to a separation space between the internal electrode and the external electrode,
    wherein the separation space, through which the aerosol particles are introduced into the apparatus for classifying particles and flow, is formed to be narrowed toward a lower aerosol flow side from an upper aerosol flow side into which the aerosol particles are introduced, and
    wherein the external electrode includes a plurality of electrode rings stacked and connected in an up and down direction, and the aerosol particles are discharged to an outside through a portion between two adjacent electrode rings of the plurality of electrode rings.

2. The apparatus of claim 1, wherein each of the electrode rings includes an electrode ring body which faces an inner surface of the internal electrode and forms the separation space, and a protruding portion which is connected to a lower end of the electrode ring body and protrudes radially outward.

3. The apparatus of claim 2, wherein a spacing protrusion, which allows the two adjacent electrode rings to be spaced apart from each other, is provided on at least one of the electrode ring body and the protruding portion, and a slit is formed between the two adjacent electrode rings by the spacing protrusion.

4. The apparatus of claim 3, comprising:
    an external housing which is provided on an outer circumferential portion of the external electrode and has an accommodating groove that accommodates at least one of the electrode rings.

5. The apparatus of claim 4, wherein a chamber, which allows the aerosol particles discharged from the separation space to remain in the chamber, is formed between at least one of the electrode rings and the external housing, and the chamber is a space formed between the electrode ring body, the protruding portion, and the accommodating groove.

6. The apparatus of claim 5, wherein at least one classified particle discharge hole, through which the aerosol particles are classified according to the size and discharged, is formed in the external housing, the separation space and the chamber are in communication with each other through the slit, and the chamber and the outside are in communication with each other through the classified particle discharge hole.

7. The apparatus of claim 1, wherein the separation space is formed to be narrowed from the upper aerosol flow side into which the aerosol particles are introduced toward the lower aerosol flow side from which the aerosol particles are discharged.

8. The apparatus of claim 1, wherein an air supply unit for supplying air to the separation space has a cap structure coupled to cover one side of the separation space between the internal electrode and the external electrode, and has one or more air supply holes formed in a sidewall of the air supply unit, the aerosol supply unit is coupled to penetrate the air supply unit, and an aerosol dispersing block for dispersing the aerosol particles is further provided at an aerosol outlet side of the aerosol supply unit.

9. A system for classifying particles, the system comprising:
    a particle classifying apparatus which has an air supply unit for supplying air, and at least one classified particle discharge hole for classifying aerosol particles according to the size and discharging the aerosol particles;
    an air saturator which is connected to the particle classifying apparatus and saturates the air to make a saturated vapor; and
    at least one condenser which is provided separately from the air saturator and connected to the particle classifying apparatus or the air saturator, and condenses the aerosol particles included in the saturated vapor.

10. The system of claim 9, wherein the number of air saturator is one, and the number of condensers is more than one so as to correspond to the number of classified particle discharge holes.

11. The system of claim 10, further comprising:
    detectors which are connected to the condensers, respectively, and detect the aerosol particles; and
    flow rate adjusters which adjust flow rates of the aerosol particles.

12. The system of claim 11, further comprising:
    a heater which is provided to surround the particle classifying apparatus and maintains a temperature of the particle classifying apparatus so that the temperature of the particle classifying apparatus is higher than or equal to a temperature of the air saturator.

13. The system of claim 9, wherein the particle classifying apparatus includes:
- an internal electrode which has a column shape;
- an external electrode which is spaced apart from the internal electrode and disposed to surround the internal electrode, and generates an electric field through an interaction with the internal electrode; and
- an aerosol supply unit which supplies the aerosol particles, and
- a separation space, through which the aerosol particles are introduced into the particle classifying apparatus and flow, is formed to be narrowed toward a lower aerosol flow side from an upper aerosol flow side into which the aerosol particles are introduced.

14. The system of claim 13, wherein the internal electrode is formed such that an outer diameter of the internal electrode is increased stepwise or gradually increased toward the lower aerosol flow side.

* * * * *